United States Patent [19]

Miyahara et al.

[11] Patent Number: 4,693,888

[45] Date of Patent: Sep. 15, 1987

[54] CARIES-PREVENTIVE COMPOSITION

[75] Inventors: Tsuneo Miyahara; Yoshihiro Harada, both of Kanagawa; Katsuyuki Futakami, Chigasaki; Yasukuni Nishida, Kanagawa; Ryoko Konishi, Ito, all of Japan

[73] Assignee: Lion Corporation, Tokyo, Japan

[21] Appl. No.: 638,553

[22] Filed: Aug. 7, 1984

[30] Foreign Application Priority Data

Aug. 11, 1983 [JP] Japan ................................ 58-146859
Aug. 11, 1983 [JP] Japan ................................ 58-146858

[51] Int. Cl.$^4$ .................. A61K 7/16; A61K 7/18; A61K 7/28
[52] U.S. Cl. ........................... 424/49; 514/835; 424/48; 424/50; 424/52; 424/57; 424/87; 424/88; 424/440; 106/35
[58] Field of Search .................. 106/35; 514/835; 424/48, 49, 50, 52, 57, 88-92, 87

[56] References Cited

U.S. PATENT DOCUMENTS

| | | | |
|---|---|---|---|
| 3,662,059 | 5/1972 | Wiesner et al. | 424/50 |
| 3,985,869 | 10/1976 | Yoshimura et al. | 424/50 |
| 4,133,875 | 1/1979 | Hillman | 424/50 |
| 4,150,116 | 4/1979 | Taubman et al. | 424/50 |
| 4,228,150 | 10/1980 | Robyt et al. | 514/835 |
| 4,324,782 | 4/1982 | Beck | 424/87 |
| 4,419,346 | 12/1983 | Stroz | 514/835 |
| 4,442,085 | 4/1984 | Colman et al. | 424/87 |
| 4,521,513 | 6/1985 | Russell | 424/87 |

FOREIGN PATENT DOCUMENTS

| | | | |
|---|---|---|---|
| 60-38327 | 2/1985 | Japan | 514/835 |
| 1375866 | 11/1974 | United Kingdom | 424/87 |

*Primary Examiner*—Ronald W. Griffin
*Attorney, Agent, or Firm*—Birch, Stewart, Kolasch and Birch

[57] ABSTRACT

A caries-preventive composition comprises an antibody obtained by immunizing a mammal with at least one antigen selected from the group consisting of Streptococcus mutans, its cell-wall fraction, fibrous substance fraction, glucosyltransferase fraction and protein antigen fraction, and a synergist selected from the group consisting of fluorine compounds, chlorhexidine and its salts, lytic enzymes, bacteriocins, glucosyltransferase inhibitors, proteases and dextranases.

27 Claims, No Drawings

CARIES-PREVENTIVE COMPOSITION

BACKGROUND OF THE INVENTION

This invention relates to a caries-preventive composition which, when applied to the mouth, can prevent dental caries by suppressing formation of dental plaque.

Dental plaque firmly adhering to the surface of teeth, is composed of about 70% bacteria, about 20% polysaccharides produced by the bacteria and about 10% food remains. It is said that acids stored in dental plaque decalcify enamel, causing dental caries. Therefore, dental plaque is observed as a cause of dental caries.

Formation of dental plaque is accelerated due to the synthesis of polysaccharides from sucrose by oral bacteria, especially *Streptococcus mutans*. More specifically, *Streptococcus mutans* synthesizes adhesive polysaccharides such as dextran and mutan from sucrose through the production of GTF (glucosyltransferase, dextran-synthesizing enzyme). The thus synthesized polysaccharides incorporate *Streptococcus mutans* as well as other bacteria (viruses), forming dental plaque having a given bacterial bouquet. In addition, bacteria such as *Streptococcus mutans* produce acids by utilizing various kinds of sugar and the thus produced acids decalcify the surface of enamel by remaining in polysaccharides and bacterial walls.

Accordingly, decreasing the number of *Streptococcus mutans* in the mouth and suppressing the formation of dental plaque is desired in order to prevent dental caries.

It is known in British Pat. No. 1,505,513 that colonization of *Streptococcus mutans* in the mouth is suppressed by using mother's milk obtained by immunizing a cow with whole bacterial bodies of *Streptococcus mutans*.

The present inventors studies antibodies which are included in the antibodies to various antigens derived *from Streptococcus mutans* and inhibit the colonization of *Streptococcus mutans* in the mouth. As a result, the inventors found that antibodies contained in antiserum and milk obtained by immunizing mammals with *Streptococcus mutans*, its cell-wall fraction, fibrous substance fraction, glucosyltransferase fraction and protein antigen fraction have certain degrees of dental-plaque-formation suppressing effect. However, the effect was not necessarily sufficient and a higher effect of suppressing the formation of dental plaque was necessary.

SUMMARY OF THE INVENTION

An object of the present invention is to provide a caries-preventive composition having an excellent effect on preventing dental caries.

For the purpose of attaining the above object, the present inventors further conducted an intensive study, and, as a result, found that the combination of said antibody and a fluorine compound, chlorhexidine or its salt, a lytic enzyme, a bacteriocin, a glucosyltransferase inhibitor, a protease or a dextranase works effectively for the prevention of dental caries by causing a significantly increased dental-plaque-formation suppressing effect through the suppression of colonization of *Streptococcus mutans*.

Therefore, this invention provides a caries-preventive composition characterized by being composed of the combination of antibody obtained by immunizing a mammal with at least one antigen selected from the group consisting of *Streptococcus mutans*, its cell-wall fraction, fibrous substance fraction, glucosyltransferase fraction and protein antigen fraction with at least one synergist selected from the group consisting of fluorine compounds, chlorhexidine and its salts, lytic enzymes, bacteriocins, glucosyltransferase inhibitors, proteases and dextranases.

According to this invention, since the combination of said antibody and said synergist component exerts a synergistic effect on the inhibition of colonization of Streptococcus mutans in the mouth, the formation of dental plaque is efficiently suppressed, resulting in the effective prevention of dental caries.

In addition, since said antibody and said synergist component both are highly safe, the caries-preventive composition according to this invention can be safely used.

The above and other objects, features, and advantages of this invention will be more fully understood by reading the following description.

DETAILED DESCRIPTION OF THE INVENTION

The caries-preventive composition according to this invention is prepared by use of antibody contained in antiserum and/or milk obtained by immunizing a mammal with at least one antigen selected from the group consisting of Streptococcus mutans, its cell-wall fraction, fibrous substance fraction, glucosyltransferase (GTF) fraction and protein antigen fraction as described above. It should be noted that the fibrous substance means a pili-like or fimbriae fraction.

*Streptococcus mutans* used as an antigen may be prepared through well-known culture and pretreatment carried out by, for example, growing bacteria in external solution obtained by the dialysis of BHI medium before the thus grown bacteria are washed and subjected to formalin treatment. *Streptococcus mutans* separated from human mouth and belonging to the serotypes C, D, E, F and G may preferably be used, particularly one being numerous in the human mouth and belonging to the serotype-C is more preferably used. Such *Streptococcus mutans* includes NCTC10449, Ingbritt, OMZ70, JC-2, etc. and their mutant strains.

The cell-wall fraction of *Streptococcus mutans* may be prepared, for example, according to the method of Bleiweis et al. (J. Bacteriol., 88, 1198–1200, 1964) by subjecting *Streptococcus mutans* to crushing treatment by use of a Brown's cell crusher and glass beads of 0.17 to 0.18 mm diameter, then treating the thus obtained cell walls with trypsin to remove protein contaminating the cell walls, being followed by washing the cell walls with distilled water before they are lyophilized. The fibrous (pili-like or fimbriae) substance fraction may be prepared, for example, according to the method of J. Van Hoate et al. (Arch. Oral. Bio., 16, 1131–1141, 1971) by culturing *Streptococcus mutans* in a medium obtained by the dialysis of BHI medium and containing 5% sucrose under an anaerobic condition, then centrifuging the culture medium to obtain a supernatant solution before three times as much ethanol as the supernatant solution by volume is added, being followed by collecting the precipitate of the thus obtained solution. As the fibrous substance fraction, a pili-like structure from the cell wall of *Streptococcus mutans* and its purified substance prepared by the ordinary cell wall extract method from the cultured bacteria using solvents such as phosphate buffer containing 1M sodium chloride according to the method of Tsurumizu et al. (Japanese Journal of Bacteriology, 38, (1) 471, 1983) may also be used. The GTF fraction may be prepared, for example, according to the method of Inoue et al. (Microbial Aspects of dental caries Vol. III, 665–682, 1976 [Information Retrieval Inc.]) by using solution prepared by the following method: after *Streptococcus mutans* is implanted and grown in a medium obtained by the dialysis of BHI medium, the bacterial bodies are removed by centrifugation and the supernatant is saturated with ammonium sulfate at the level of 40%, followed by dialyzing the precipitate of the 40% ammonium sulfate fraction against 50 mM phosphate buffer solution and concentrating or diluting the obtained solution. The protein antigen fraction may be prepared, for example, according to the method of Lehner et al. (J. General Microbiology, 122, 217–225, 1981) by culturing *Streptococcus mutans* in a medium obtained by the dialysis of BHI medium before the culture medium is centrifuged to obtain a supernatant solution prior to it being fractionated with 75% ammonium sulfate solution to collect the precipitate, then subjecting the thus obtained precipitate to DE-52 column chromatography under the existence of 6M urea before the protein antigen fraction is dissolved in physiological saline, being followed by dialyzing thus obtained solution before the dialyzed solution is subjected to gel filtration through Sepharose CL6B.

The usual method may be adopted in immunizing mammals with said antigens. As mammals to be immunized, goats, sheep, horses, cows, rabbits, etc. may be used.

The antibody (protein fraction in the antiserum and the milk) may be separated from the antiserum and the milk according to the ordinary antibody purification method including the salting-out method, the gel-filtration method, ion-exchange chromatography, affinity chromatography, and the like, the salting-out method using ammonium sulfate being preferred. In the salting-out method, the antiserum or the milk is saturated with ammonium sulfate preferably at the level of not more than 40% to produce the precipitate, followed by dialyzing the precipitate against physiological saline to obtain the purified precipitate as the antibody. The preferred antibody is obtained from the equine antiserum and the bovine antiserum and milk.

In this invention, the antibody contained in the antiserum and milk obtained by immunizing the mammal with said antigen is blended to the composition. In this case, the antiserum and milk as well as the antibody separated and purified from the antiserum and milk may be used. Each of these matters may be used alone or in a combination of two or more.

The caries-preventive composition according to this invention is prepared by the combination of said antibody and at least one synergist selected from the group consisting of fluorine compounds, chlorhexidine and its salts, lytic enzymes, bacteriocins, glucosyltransferase inhibitors, proteases and dextranases.

As fluorine compounds, sodium fluoride, potassium fluoride, lithium fluoride, ammonium fluoride, sodium monofluorophosphate, sodium hydrogen monofluorophosphate, potassium monofluorophosphate, ammonium monofluorophosphate, potassium hexafluorozirconate, and potassium hexafluorotitanate may be used. Also useful are cesium fluoride, nickel fluoride, zirconium fluoride, silver fluoride, hexylamine hydrofluoride, laurylamide hydrofluoride, cetylamine hydrofluoride, glycine hydrofluoride, lysine hydrofluoride, alanine hydrofluoride and the like. Among them, monofluorophosphates such as sodium monofluorophosphate and potassium monofluorophosphate, alkali-metal fluorides such as sodium fluoride, potassium fluoride and ammonium fluoride, fluorides containing stannous tin such as stannous fluoride and stannous chloride fluoride and the like may preferably be used. Especially, sodium monofluorophosphate, sodium fluoride and stannous fluoride are more preferably used.

As chlorhexidine and its salts, chlorhexidine hydrochloride, chlorhexidine gluconate, etc. are used.

As lytic enzymes, those derived from *Streptomyces griseus, Streptomyces diastatochromagenes, Streptomyces farinosus*, Chalaropsis, Flavobacterium, Myxobacter, *Staphylococcus epidermidis*, Micrococcus, *Pseudomonas aetuginosa*, Aeromanas, *Streptomyces albus, Streptomyces globisporus*, etc. can be used.

As bacteriocins, those derived from *Enterobactor cloacae, Escherichia coli, Proteus micrabilis, Pseudomonas aeruginosa, Streptococcus mutans, Staphylococcus staphylolyticus*, etc. can be used.

As GTF inhibitors, those derived from Arthrinum sp., Fusarinum sp., Macrophomina sp., Micromonospora sp., Gnomoniella sp., Nodulisporium sp., Aspergillus sp., etc. can be used, and more specifically, those described in Japanese Patent Application Laid-Open Nos. 56-103193, 57-28097, 57-98215, and 57-146587 can be used.

As proteases, those derived from Aspergillus sp., Bacillus sp., etc. can be used.

As dextranases, those derived from Chaetomium sp., Streptomyces sp., Bacillus sp., Corynebacterium, etc. can be used.

In this invention, each of these synergist components may be used alone or in a combination of one or two.

The caries-preventive composition according to this invention can be prepared and used in various forms applicable to the mouth such as dentifrices (including toothpaste, toothpowder and liquid dentifrice), mouthwashes, dental pastes, gingival massage creams, gargle tablets, troches, chewing gums, ice-creams, whipped creams and the like.

The antibody and the synergist component may be mixed in a given form. Alternatively, the antibody and the synergist component may be jointly used after they are prepared separately.

It is preferred that the quantity of said antibody administered is 0.0001 to 50 g/kg/day. As to the quantity of said synergist component administered, a quantity corresponding to 0.0001 to 1 g/kg/day fluorine for fluorine compounds, a quantity corresponding to 0.0001 to 1 g/kg/day chlorhexidine for chlorhexidine and its salts, a quantity of 0.0001 to 10 g/kg/day each for lytic enzymes, bacteriocins and glucosyltransferase inhibitors and a quantity of 0.0001 to 5 g/kg/day each for proteases and dextranases are preferably used. The blended amount of the antibody to the oral composition may be in the range of 0.0002 to 10%, preferably 0.002 to 5% by weight of the total weight of the composition. As to the blended amount of the synergist component in the composition, it is preferred that an amount corresponding to 0.0001 to 0.1 wt%, preferably 0.0001 to 0.001 wt% fluorine for fluorine compounds; an amount corresponding to 0.1 to 1000 ppm, preferably 10 to 100 ppm chlorhexidine for chlorhexidine and its salts; and an amount of 0.0001 to 10 wt%, preferably 0.001 to 5 wt% each for lytic enzymes, bacteriocins, glucosyltransferase inhibitors, proteases and dextranases may be blended to the composition.

The oral composition according to this invention may further include additional well-known ingredients depending on the type and form of a particular oral composition. Any desired known ingredients may be mixed with said antibody and synergist component.

In preparing dentifrice compositions, an abrasive may be blended generally in an amount of 5 to 95%, especially 15 to 60% by weight of the composition, including calcium secondary phosphate dihydrate, calcium secondary phosphate anhydrate, calcium primary phosphate, calcium tertiary phosphate, calcium carbonate, calcium pyrophosphate, insoluble sodium metaphosphate, amorphous silica, crystal silica, aluminosilicate, aluminum oxide, aluminum hydroxide, magnesium tertiary phosphate, magnesium carbonate, calcium sulfate, titanium dioxide, resins, and the like.

In preparing paste-like compositions, typically toothpastes, a binder may be blended generally in an amount of 0.3 to 5% by weight, including sodium carboxymethyl cellulose, methyl cellulose, sodium carboxymethyl hydroxyethyl cellulose, hydroxyethyl cellulose, sodium alginate, carrageenan, gum arabic, xanthan gum, tragacanth gum, karaya gum, polyvinylalcohol, sodium polyacrylate, carboxyvinyl polymer, polyvinyl pyrrolidone, and the like.

In preparing paste-like and liquid oral compositions, typically toothpastes and mouthwashes, a humectant may be blended generally in an amount of 10 to 70% by weight, including polyethylene glycol, ethylene glycol, sorbitol, glycerol, propylene glycol, 1,3-butylene glycol, xylitol, maltitol, lactitol, and the like.

In addition to the above ingredients, a surface active agent including water soluble salts of alkyl sulfate having 8 to 18 carbon atoms such as sodium laurate and sodium myristate, sodium salts of higher fatty acids, water-soluble salts of sulfonated monoglycerides of higher fatty acids having 10 to 18 carbon atoms in the fatty acid group such as sodium lauryl monoglyceride sulfonate and sodium coconut monoglyceride sulfonate, sodium monoglyceride monosulfates of higher fatty acids, olefin sulfonates, paraffin sulfonates, sodium N-methyl-N-palmitoyl touride, sodium N-lauroyl sarcosinate, sodium N-lauroyl-β-alanine, include alkyrol mono- and di-ethanol amides such as lauroyl mono- and di-ethanol amides, stearyl monoglyceride, sucrose fatty acid esters having 12 to 18 carbon atoms in the fatty acid group such as sucrose monolaurate and dilaurate, lactose fatty acid esters, lactitol fatty acid esters, maltitol fatty acid esters, stearic acid monoglyceride, polyoxyethylene sorbitan monolaurate, polyoxyethylene-hardened castor oil, condensates of sorbitan monostearate with approximately 60 moles of ethylene glycol, condensates of ethylene oxide with propylene oxide, and their derivatives such as polyoxyethylene polyoxypropylene monolauryl ester, betaine and amino acid type amphoteric surfactants, and the like may be blended in an amount of 0 to 10%, preferably 0.1 to 5%, more preferably 1 to 2.5% by weight of the composition. A flavor such as an essential oil including peppermint oil and spearmint oil and a flavoring material including l-menthol, carvone, eugenol and anethole, a sweetener such as sodium saccharinate, stevioside, neohesperidyldihydrochalcone, glycyrrhizin, perillartine, p-methoxycinnamic aldehyde, a preservative, and the like may be blended in an effective amount.

In this invention, effective ingredients such as mutanase, sorbic acid, alexidine, hinokitiol, cetylpyridinium chloride, alkyl glycine, alkyldiaminoethyl glycinate, allantoin, ε-aminocaproic acid, tranexamic acid, azulene, vitamin E, a water soluble primary or secondary phosphate, a quaternary ammonium compound, sodium chloride and crude drugs may also be blended in an effective amount.

Other types of compositions may also be prepared by selecting any desired ingredients as usual and mixing them by a conventional procedure.

Examples of the other ingredients for various types of forms of the composition are shown in the following Examples.

Paste-like and liquid oral compositions may generally have a pH ranging from 5 to 10, but not limited thereto.

The caries-preventive composition according to this invention, owing to the combination of said antibody and said synergist component, can efficiently suppress the formation of plaque caused by *Streptococcus mutans*, thereby excellently preventing the formation of dental caries.

Examples of this invention will be given in the following although this invention is not restricted to them.

EXAMPLE 1

Antisera and mother's milks were obtained by using the following antigens according to the following method.

(1) Antigens

*Streptococcus mutans* NCTC10449

Bacteria grown in the external solution obtained by the dialysis of BHI medium, after being washed, were treated with formalin before being supplied for use.

Cell-wall fraction of *Streptococcus mutans* NCTC10449

The fraction prepared according to the method of Bleiweis et al. (J. Bacteriol., 88, 1198–1200, 1964) was supplied for use.

Fibrous substance fraction of *Streptococcus mutans* NCTC10449

The fraction prepared according to the method of J. Van Hoate et al. (Arch. Oral. Bio., 16, 1131–1141, 1971) and Tsurumizu et al (Jap. J. Bacteriology, 38, (1) 471, 1983) were supplied for use.

Glucosyltransferase fraction of *Streptococcus mutans* NCTC10449

The fraction prepared according to the method of Inoue et al. (Microbial Aspects of dental caries Vol. III, 665–682, 1976 [Information Retrieval Inc.]) was supplied for use.

Protein antigen fraction of *Streptococcus mutans* NCTC10449

The fraction prepared according to the method of Lehner et al. (J. General Microbiology, 122, 217–225, 1981) was supplied for use.

(2) Preparation of Antiserum and Mother's Milk

Said antigen was mixed with Freund's complete adjuvant, and a pregnant goat, horse, cow or rabbit was immunized with the thus prepared mixture. After the animal was immunized three times with the mixture of said antigen and Freund's incomplete adjuvant before its delivery, the colostrum was collected after the delivery. As to the antiserum, after the animal was immunized four times in the same manner as above, the blood was collected and coagulated, and supernatant solution obtained by centrifuging the coagulated blood was used as a sample.

An antibody is prepared by adding ammonium sulfate to the antiserum to saturate it at the level of 40%, separating the obtained precipitate by centrifugation, dialyzing the precipitate against physiological saline, and the inner solution was used as a sample.

Next, the colonizing tests of *Streptococcus mutans* in the mouth were conducted according to the following method by using said antiserum and mother's milk as well as a fluorine compound, a chlorhexidine salt, a lytic enzyme, a bacteriocin, GTF inhibitors, a protease and a dextranase used as synergist components.

(3) Colonization of *Streptococcus mutans* in the Mouth

After male hamsters of five week old were divided into groups each consisting of five individuals, each hamster was inoculated with $1 \times 10^8$ bacteria of *Streptococcus mutans* of the NCTC10449 strain. From the day of the inoculation, drinking water containing the effective components (said antiserum or milk and the synergist component) was administered to each hamster. One week and four weeks after the start of the administration, the teeth of each hamster were rubbed with a cotton ball before it is immersed in a small amount of physiological saline to disperse bacteria homogeneously in it. After a given amount of the thus obtained solution was scattered on the BHI plate medium and the mitts salivalius plate medium, the number of whole bacteria and the number of the colonies of *Streptococcus mutans* were counted. The number of *Streptococcus mutans* was indicated by the number of *Streptococcus mutans* per 10,000 whole bacteria. The concentration of antiserum or mother's milk in the drinking water was adjusted to 0.025%. As to the concentration of the synergist component, it was adjusted to 0.05% for a fluorine compound (NaF), 0.005% for a chlorhexidine salt (chlorhexidine gluconate), 0.05% for a lytic enzyme, 0.01% each for a bacteriocin, a GTF inhibitor and a protease and 0.005% for a dextranase.

For comparison, the same experiments were conducted without jointly using antiserum or mother's milk and the synergist component by adding antiserum or mother's milk alone, by adding the synergist component alone and by adding none of antiserum, mother's milk and the synergist component (Control).

The results obtained by using the fluorine compound (NaF) as the synergist component are indicated in Table 1; those obtained by using chlorhexidine gluconate (CHX), in Table 2; those obtained by using the lytic enzyme, in Table 3; those obtained by using the bacteriocin, in Table 4; those obtained by using the GTF inhibitors, in Table 5; those obtained by using the protease, in Table 6; and those obtained by using the dextranase, in Table 7.

TABLE 1

| Samples Added | Number of S. mutans bacteria 1 week after | Number of S. mutans bacteria 4 weeks after |
| --- | --- | --- |
| Control | 3890 | 4250 |
| Goat anti-whole-bacteria serum | 2178 | 1467 |
| Goat anti-whole bacteria serum + NaF | 1945 | 297 |
| Goat anti-GTF serum | 1828 | 1510 |
| Goat anti-GTF serum + NaF | 1556 | 212 |
| Goat anti-whole-bacteria mother's milk | 1984 | 1382 |
| Goat anti-whole-bacteria mother's milk + NaF | 1945 | 170 |
| Goat anti-cell-wall serum | 1750 | 1340 |
| Goat anti-cell-wall serum + NaF | 1750 | 255 |
| Goat anti-protein serum | 1984 | 1255 |
| Goat anti-protein serum + NaF | 1945 | 85 |
| Goat anti-fibrous-substance milk | 1945 | 1340 |
| Goat anti-fibrous-substance milk + NaF | 1711 | 27 |
| NaF alone | 3112 | 2040 |

TABLE 2

| Samples Added | Number of S. mutans bacteria 1 week after | Number of S. mutans bacteria 4 weeks after |
| --- | --- | --- |
| Control | 3890 | 4250 |
| Antibody from equine anti-whole-bacteria serum | 2139 | 1425 |
| Antibody from equine anti-whole-bacteria serum + CHX | 2139 | 212 |
| Antibody from equine anti-GTF serum | 1789 | 1297 |
| Antibody from equine anti-GTF serum + CHX | 1634 | 340 |
| Equine anti-whole-bacteria mother's milk | 1945 | 1340 |
| Equine anti-whole-bacteria mother's milk + CHX | 1984 | 170 |
| Equine anti-cell-wall serum | 2022 | 1425 |
| Equine anti-cell-wall serum + CHX | 1867 | 297 |
| Equine anti-protein serum | 2023 | 1425 |
| Equine anti-protein serum + CHX | 1945 | 212 |
| Equine anti-fibrous-substance milk | 1867 | 1383 |
| Equine anti-fibrous-substance milk + CHX | 1134 | 85 |
| CHX alone | 3112 | 2975 |

TABLE 3

| Samples Added | Number of S. mutans bacteria 1 week after | Number of S. mutans bacteria 4 weeks after |
| --- | --- | --- |
| Control | 3890 | 4250 |
| Bovine anti-whole-bacteria serum | 2178 | 1425 |
| Bovine anti-whole-bacteria serum + Lytic enzyme | 1945 | 255 |
| Bovine anti-GTF serum | 1828 | 1382 |
| Bovine anti-GTF serum + Lytic enzyme | 1556 | 340 |
| Bovine anti-whole-bacteria mother's milk | 2023 | 1298 |
| Bovine anti-whole-bacteria mother's milk + Lytic enzyme | 1945 | 127 |
| Antibody from bovine anti-cell-wall serum | 2139 | 1255 |
| Antibody from bovine anti-cell-wall serum + Lytic enzyme | 1867 | 85 |

TABLE 3-continued

| Samples Added | Number of S. mutans bacteria 1 week after | Number of S. mutans bacteria 4 weeks after |
|---|---|---|
| Bovine anti-protein serum | 1556 | 1085 |
| Bovine anti-protein serum + Lytic enzyme | 1556 | 42 |
| Bovine anti-fibrous substance milk | 2334 | 1298 |
| Bovine anti-fibrous substance milk + Lytic enzyme | 1984 | 85 |
| Lytic enzyme alone | 3112 | 3485 |

(Note) As the lytic enzyme, one obtained from *Streptomyces globisporus* was used.

TABLE 4

| Samples Added | Number of S. mutans bacteria 1 week after | Number of S. mutans bacteria 4 weeks after |
|---|---|---|
| Control | 3890 | 4250 |
| Rabbit anti-whole-bacteria serum | 2178 | 1383 |
| Rabbit anti-whole-bacteria serum + Bacteriocin | 2100 | 298 |
| Rabbit anti-GTF serum | 1556 | 1467 |
| Rabbit anti-GTF serum + Bacteriocin | 1634 | 255 |
| Rabbit anti-whole-bacteria mother's milk | 1945 | 1510 |
| Rabbit anti-whole-bacteria mother's milk + Bacteriocin | 1945 | 213 |
| Rabbit anti-cell-wall serum | 2023 | 1595 |
| Rabbit anti-cell-wall serum + Bacteriocin | 1634 | 170 |
| Rabbit anti-protein serum | 1945 | 1298 |
| Rabbit anti-protein serum + Bacteriocin | 1751 | 128 |
| Rabbit anti-fibrous-substance milk | 2178 | 1383 |
| Rabbit anti-fibrous substance milk + Bacteriocin | 1751 | 128 |
| Bacteriocin alone | 2723 | 3060 |

(Note) As the bacteriocin, one obtained from Streptococcus L-1, microbial technology research laboratory trust number 3220, was used.

TABLE 5

| Samples Added | Number of S. mutans bacteria 1 week after | Number of S. mutans bacteria 4 weeks after |
|---|---|---|
| Control | 3890 | 4250 |
| Goat anti-whole-bacteria serum | 2188 | 1425 |
| Goat anti-whole-bacteria serum + GTF inhibitor A | 2100 | 212 |
| Goat anti-GTF serum | 1867 | 1297 |
| Gaot anti-GTF serum + GTF inhibitor A | 1789 | 176 |
| Goat anti-whole-bacteria mother's milk | 1945 | 1340 |
| Goat anti-whole-bacteria mother's milk + GTF inhibitor B | 1828 | 85 |
| Goat anti-cell-wall serum | 2022 | 1425 |
| Goat anti-cell-wall serum + inhibitor A | 1945 | 340 |
| Goat anti-protein serum | 1945 | 1297 |
| Goat anti-protein serum + GTF inhibitor C | 1906 | 255 |
| Goat anti-fibrous substance milk | 2178 | 1383 |
| Goat anti-fibrous substance milk + GTF inhibitor A | 1751 | 185 |
| GTF inhibitor A alone | 2723 | 3485 |
| GTF inhibitor B alone | 3112 | 3400 |
| GTF inhibitor C alone | 2995 | 3315 |

(Note)
GTF inhibitor A was obtained from *Aspergillus terreus*;
GTF inhibitor B, from Arthrinum sp. M 5071; and
GTF inhibitor C, from Micromonospora sp. SF-2259.

TABLE 6

| Samples Added | Number of S. mutans bacteria 1 week after | Number of S. mutans bacteria 4 weeks after |
|---|---|---|
| Control | 3890 | 4250 |
| Equine anti-whole-bacteria serum | 2334 | 1297 |
| Equine anti-whole-bacteria serum + Protease | 2022 | 85 |
| Equine anti-GTF serum | 1867 | 1340 |
| Equine anti-GTF serum + Protease | 1789 | 85 |
| Equine anti-whole-bacteria mother's milk | 2022 | 1382 |
| Equine anti-whole-bacteria mother's milk + Protease | 1867 | 42 |
| Equine anti-cell-wall serum | 2178 | 1510 |
| Equine anti-cell-wall serum + Protease | 2022 | 170 |
| Equine anti-protein serum | 1945 | 1552 |
| Equine anti-protein serum + Protease | 1711 | 42 |
| Equine anti-fibrous-substance milk | 2100 | 1340 |
| Equine anti-fibrous-substance milk + Protease | 1634 | 170 |
| Protease alone | 3034 | 3655 |

(Note) The protease used is derived from Aspergillus sp.

TABLE 7

| Samples Added | Number of S. mutans bacteria 1 week after | Number of S. mutans bacteria 4 weeks after |
|---|---|---|
| Control | 3890 | 4250 |
| Bovine anti-whole-bacteria serum | 2334 | 1297 |
| Bovine anti-whole-bacteria serum + Dextranase | 2100 | 212 |
| Bovine anti-GTF serum | 2022 | 1510 |
| Bovine anti-GTF serum + Dextranase | 1789 | 212 |
| Bovine anti-whole-bacteria mother's milk | 2139 | 1552 |
| Bovine anti-whole-bacteria mother's milk + Dextranase | 1945 | 340 |
| Bovine anti-cell-wall serum | 2139 | 1595 |
| Bovine anti-cell-wall serum + Dextranase | 1828 | 85 |
| Bovine anti-protein serum | 2022 | 1297 |
| Bovine anti-protein serum + Dextranase | 1983 | 170 |
| Bovine anti-fibrous | 1867 | 1383 |

TABLE 7-continued

| Samples Added | Number of S. mutans bacteria 1 week after | Number of S. mutans bacteria 4 weeks after |
|---|---|---|
| substance milk | | |
| Bovine anti-fibrous substance milk + Dextranase | 1634 | 85 |
| Dextranase alone | 2022 | 1275 |

(Note) The dextranase used is derived from Chetomium sp.

From the results indicated in Tables 1 to 7, it is found that the combination of the antiserum or mother's milk and the synergist component according to this invention excellently suppresses the colonization of Streptococcus mutans.

EXAMPLE 2 Toothpaste

| | |
|---|---|
| Calcium secondary phosphate dihydrate | 50.0% |
| Glycerol | 20.0 |
| Sodium carboxymethylcellulose | 1.0 |
| Sodium lauryl sulfate | 1.5 |
| Sodium lauroyl sarcosinate | 0.5 |
| Flavor | 1.0 |
| Sodium saccharinate | 0.1 |
| Water | Balance |
| | 100.0% |

The above components were blended with 0.1% or 0.2% antibody of goat whole-bacteria and 0.1% sodium fluoride, 0.01% chlorhexidine gluconate, 0.1% a lytic enzyme, 0.01% a bacteriocin, 0.001% a protease, 0.1% GTF inhibitor-A or 0.25% (3000 units/g) a dextranase.

EXAMPLE 3 Toothpaste

| | |
|---|---|
| Calcium secondary phosphate | 50.0% |
| Sorbitol | 10.0 |
| Glycerol | 10.0 |
| Sodium carboxymethylcellulose | 1.0 |
| Sodium lauryl sulfate | 2.0 |
| Flavor | 1.0 |
| Sodium saccharinate | 0.1 |
| Ethanol | 2.0 |
| Mutanase | 0.1 |
| Water | Balance |
| | 100.0% |

The above components were blended with 0.1% bovine anti-cell-wall serum and 0.3% sodium monofluorophosphate, 0.01% chlorhexidine gluconate, 0.05% a lytic enzyme, 0.02% a bacteriocin, 0.001% a protease, 0.1% GTF inhibitor-C or 0.25% a dextranase.

EXAMPLE 4 Toothpaste

| | |
|---|---|
| Calcium carbonate | 50.0% |
| Glycerol | 20.0 |
| Carrageenan | 0.5 |
| Sodium carboxymethylcellulose | 1.0 |
| Lauroyl diethanolamide | 1.5 |
| Sucrose monolaurate | 2.0 |
| Flavor | 1.0 |
| Sodium saccharinate | 0.1 |
| Water | Balance |
| | 100.0% |

The above components were blended with 0.05% bovine anti-GTF mother's milk and 0.1% sodium fluoride, 0.005% chlorhexidine gluconate, 0.1% a lytic enzyme, 0.01% a bacteriocin, 0.001% a protease, 0.1% GTF inhibitor-B or 0.25% a dextranase.

EXAMPLE 5 Toothpaste

| | |
|---|---|
| Calcium secondary phosphate dihydrate | 50.0% |
| Glycerol | 20.0 |
| Sodium carboxymethylcellulose | 2.0 |
| Sodium lauryl sulfate | 2.0 |
| Flavor | 1.0 |
| Sodium saccharinate | 0.1 |
| Water | Balance |
| | 100.0% |

The above components were blended with 0.1% equine anti-protein serum and 0.1% stannous fluoride, 0.01% chlorhexidine gluconate, 0.05% a lytic enzyme, 0.01% a bacteriocin, 0.001% a protease, 0.1% a GTF inhibitor or 0.25% a dextranase.

EXAMPLE 6 Toothpaste

| | |
|---|---|
| Silicic anhydride | 30.0% |
| Glycerol | 30.0 |
| Sorbitol | 20.0 |
| Sodium carboxymethylcellulose | 1.0 |
| Sodium lauryl sulfate | 2.0 |
| Flavor | 1.0 |
| Sodium saccharinate | 0.1 |
| Ethanol | 2.0 |
| Water | Balance |
| | 100.0% |

The above components were blended with 0.1% sheep anti-protein serum and 0.1% stannous fluoride, 0.01% chlorhexidine gluconate, 0.1% a lytic enzyme, 0.01% a bacteriocin, 0.0001% a protease, 0.1% GTF inhibitor-A or 0.17% (2000 units/g) a dextranase.

EXAMPLE 7 Toothpowder

| | |
|---|---|
| Calcium secondary phosphate dihydrate | 50.0% |
| Calcium carbonate | 30.0 |
| Glycerol | 10.0 |
| α-olefin sulfonate | 1.0 |
| Flavor | 1.0 |
| Sodium saccharinate | 0.1 |
| Dextran | 0.5 |
| Water | Balance |
| | 100.0% |

The above components were blended with 0.1% sheep anti-fibrous-substance serum and 0.1% sodium monofluorophosphate and 0.1% sodium fluoride, 0.01% chlorhexidine gluconate, 0.05% a lytic enzyme, 0.001% a bacteriocin, 0.0001% a protease, 0.1% GTF inhibitor or 0.17% a dextranase.

EXAMPLE 8 Liquid Dentifrice

| | |
|---|---|
| Sodium polyacrylate | 50.0% |
| Glycerol | 30.0 |
| Flavor | 0.9 |
| Sodium saccharinate | 0.1 |
| Ethanol | 3.0 |
| Linolic acid | 0.05 |
| Water | Balance |
| | 100.0% |

The above components were blended with 0.01% or 0.02% goat anti-GTF mother's milk and 0.01% or 0.02% goat anti-protein mother's milk and 0.02% sodium fluoride, 0.05% chlorhexidine gluconate, 0.05% a lytic enzyme, 0.001% a bacteriocin, 0.002% a protease, 0.02% GTF inhibitor-A or 0.25% a dextranase.

| EXAMPLE 9 Mouthwash | |
|---|---|
| Ethanol | 20.0% |
| Flavor | 1.0 |
| Sodium saccharinate | 0.05 |
| Lauroyl diethanolamide | 0.3 |
| Water | Balance |
| | 100.0% |

The above components were blended with 0.1% goat anti-GTF serum and 0.1% sodium monofluorophosphate and 0.01% stannous fluoride, 0.01% chlorhexidine gluconate, 0.05% a lytic enzyme, 0.001% a bacteriocin, 0.01% a protease, 0.01% GTF inhibitor-B or 0.25% a dextranase.

| EXAMPLE 10 Mouthwash (tablet) | |
|---|---|
| Sodium hydrogencarbonate | 54.0% |
| Sodium secondary phosphate | 10.0 |
| Polyethylene glycol | 3.0 |
| Citric acid | 17.0 |
| Sodium sulfate (anhydrous) | 13.6 |
| Flavor | 2.0 |
| Oleic acid | 0.1 |
| | 100.0% |

The above components were blended with 0.1% rabbit anti-GTF serum and 0.1% sodium monofluorophosphate and 0.05% sodium fluoride, 0.05% chlorhexidine gluconate, 0.05% a lytic enzyme, 0.01% a bacteriocin, 0.005% a protease, 0.05% GTF inhibitor-A or 0.25% a dextranase.

The tablet is used by dissolving 0.5 g of the tablet into 50 ml of water.

| EXAMPLE 11 Gingival Massage Cream | |
|---|---|
| White petrolatum | 8.0 |
| Propylene glycol | 4.0 |
| Stearyl alcohol | 8.0 |
| Polyethylene glycol 4000 | 25.0 |
| Polyethylene glycol 400 | 37.0 |
| Sucrose stearate | 0.5 |
| Water | Balance |
| | 100.0% |

The above components were blended with 0.5% bovine anti-fibrous-substance mother's milk and 0.5% sodium fluoride, 0.01% chlorhexidine gluconate, 0.05% a lytic enzyme, 0.01% a bacteriocin, 0.0% a protease, 0.5% GTF inhibitor-A or 0.25% a dextranase.

| EXAMPLE 12 Chewing Gum | |
|---|---|
| Gum base | 43.85% |
| Calcium carbonate | 2.0 |
| Starch syrup | 15.0 |
| Sugar | 30.0 |
| Sucrose palmitate | 1.0 |
| Fructose | 4.0 |
| Maltose | 3.0 |
| Flavor | 1.0 |
| | 100.0% |

The above components were blended with 0.1% bovine anti-whole-bacterial-body mother's milk and 0.1% stannous fluoride, 0.01% chlorhexidine gluconate, 0.1% a lytic enzyme, 0.01% a bacteriocin, 0.001% a protease, 0.1% GTF inhibitor-C or 0.25% a dextranase.

| EXAMPLE 13 Troche | |
|---|---|
| Gum arabic | 6.0 |
| Grape sugar | 72.0 |
| Gelatin | 3.0 |
| Flavor | 0.2 |
| l-menthol | 0.1 |
| Spearmint oil | 0.1 |
| Sodium ascorbate | 0.1 |
| Water | Balance |
| | 100.0% |

The above components were blended with 0.05% or 0.1% goat anti-protein serum and 0.05% sodium fluoride, 0.01% chlorhexidine gluconate, 0.05% a lytic enzyme, 0.01% a bacteriocin, 0.005% a protease, 0.1% GTF inhibitor-C or 0.25% a dextranase.

| EXAMPLE 14 Dental Paste | |
|---|---|
| Polyoxyethylene monostearate | 2.0% |
| Sorbitan monooleate | 2.0 |
| Cetyl alcohol | 2.0 |
| Palmityl alcohol | 3.0 |
| Propylene glycol | 15.0 |
| Carboxymethylcellulose | 5.0 |
| Gelatin | 1.0 |
| Saccharine | 0.2 |
| Peppermint oil | 0.5 |
| Spearmint oil | 0.5 |
| Lysozyme chloride | 5000 units/g |
| Water | Balance |
| | 100.0% |

The above components were blended with 0.05% or 0.1% equine anti-GTF serum and 0.05% sodium fluoride, 0.01% chlorhexidine hydrochloride, 0.05% a lytic enzyme, 0.01% a bacteriocin, 0.005% a protease, 0.1% GTF inhibitor-A or 0.25% a dextranase.

| EXAMPLE 15 Dental Paste | |
|---|---|
| Glyceryl monolaurate | 3.0% |
| Oleyl alcohol | 5.0 |
| Polyethylene glycol | 15.0 |
| White petrolatum | 3.0 |
| N—palmitoyl monosodium glutamate | 0.5 |
| Hydroxyethylcellulose | 5.0 |
| Tocopheryl acetate | 0.1 |
| Sodium saccharinate | 0.2 |
| Japanese peppermint oil | 0.7 |
| Carvone | 0.5 |
| Anethole | 0.3 |
| Eugenol | 0.1 |
| Water | Balance |
| | 100.0% |

The above components were blended with 0.025% or 0.05% rabbit anti-fibrous-substance serum and 0.05% sodium fluoride, 0.01% chlorhexidine hydrochloride, 0.05% a lytic enzyme, 0.001% a bacteriocin, 0.0025% a protease, 0.05% GTF inhibitor-B or 0.25% a dextranase.

| EXAMPLE 16 Ice-cream | |
|---|---|
| Cream (fat content, 50%) | 16.84% |
| Milk (fat content, 3.7%)* | 42.65 |
| Defatted evaporated milk | 24.24 |

-continued

| EXAMPLE 16 Ice-cream | |
|---|---|
| Sugar | 11.25 |
| Corn syrup | 4.65 |
| Stabilizer | 0.35 |
| | 100.0% |

*Containing 0.5% bovine anti-fibrous-substance mother's milk

The above components were blended with 0.05% a lytic enzyme or 0.05% a bacteriocin.

| EXAMPLE 17 Ice-cream | |
|---|---|
| Cream (fat content, 59%) | 16.84% |
| Milk (fat content, 3.7%)* | 42.65 |
| Defatted evaporated milk | 24.24 |
| Sugar | 11.25 |
| Corn syrup | 4.65 |
| Stabilizer | 0.35 |
| | 100.00% |

*Containing 3% bovine anti-fibrous-substance mother's milk

The above components were blended with 0.001% a protease, 0.002% GTF inhibitor-C or 0.021% (250 units/g) a dextranase.

| EXAMPLe 18 Ice-cream | |
|---|---|
| Cream (fat content, 40%) | 31.54% |
| Milk (fat content, 3.7%)** | 37.16 |
| Defatted evaporated milk | 15.08 |
| Sugar | 11.25 |
| Corn syrup | 4.67 |
| Stabilizer | 0.30 |
| | 100.00% |

**Containing 5% bovine anti-protein mother's milk.

The above components were blended with 0.05% a lytic enzyme, 0.05% a bacteriocin, 0.001% a protease, 0.1% GTF inhibitor-A or 0.42% (5000 units/g) a dextranase.

What is claimed is:

1. A caries-preventive composition, comprising:
   an effective amount of antibody obtained by immunizing a mammal with at least one antigen selected from the group consisting of Streptococcus mutans, its cell-wall fraction, it's fibrous substance fraction, it's glucosyltransferase fraction and it's protein antigen fraction; and
   an effective amount of at least one synergist selected from the group consisting of fluorine compounds, chlorhexidene and salts thereof, lytic enzymes, bacteriocins, glucosyltransferase inhibitors, proteases and dextranases.

2. The composition as claimed in claim 1, wherein Streptococcus mutans is one belonging to the serotype C or mutants thereof separated from human mouth.

3. The composition as claimed in claim 1, wherein the antibody is obtained from equine antiserum.

4. The composition as claimed in claim 1, wherein the antibody is obtained from bovine antiserum or milk.

5. The composition as claimed in claim 1, wherein the antibody is prepared from the precipitate obtained by saturating the antiserum or milk with ammonium sulfate at the level of not more than 40%.

6. The composition as claimed in claim 1, wherein the blending amount of the antibody is in the range of 0.0002 to 10% by weight of the composition.

7. The composition as claimed in claim 1, wherein the fluorine compound is selected from the group consisting of monofluorophosphates, alkali-metal fluorides, fluorides containing stannous tin, and mixtures thereof.

8. The composition as claimed in claim 7, wherein the fluorine compound is selected from the group consisting of sodium monofluorophosphate, sodium fluoride, stannous fluoride, and mixtures thereof.

9. The composition as claimed in claim 1, wherein the blending amount of the fluoride compound is in the range of 0.0001 to 0.1% by weight of the composition as fluorine.

10. The composition as claimed in claim 1, wherein the chlorhexidine salt is selected from the group consisting of chlorhexidine hydrochloride, chlorhexidine gluconate, and a mixture thereof.

11. The composition as claimed in claim 1, wherein the blending amount of chlorhexidine and its salts is in the range of 0.1 to 1000 ppm.

12. The composition as claimed in claim 1, wherein the blending amount of the synergist selected from the group consisting of lytic enzymes, bacteriocins, glucosyltransferase inhibitors, proteases and dextranases is in the range of 0.0001 to 10% by weight of the composition.

13. The composition as claimed in claim 7, wherein the composition is prepared as a dentifrice, a mouthwash, an oral paste or a gingival massage cream.

14. The composition as claimed in claim 12, wherein the composition is prepared as a troche or a chewing gum.

15. The composition as claimed in claim 12, wherein the composition is prepared as an ice cream.

16. The composition as claimed in claim 1, wherein the ;i Streptococcus mutans is selected from the group consisting of serotypes D, E, F and G separated from the human mouth.

17. The composition as claimed in claim 1, wherein the antibody is obtained by immunizing a mammal selected from the group consisting of goats, sheep, horses, cows and rabbits.

18. The composition as claimed in claim 1, wherein the fluorine compounds are selected from the group consisting of sodium fluoride, potassium fluoride, lithium fluoride, ammonium fluoride, sodium monofluorophosphate, sodium hydrogen monofluorophosphate, potassium monofluorophosphate, ammonium monofluorophosphate, potassium hexafluorozircohate, potassium hexafluorotitanate, cesium fluoride, nickel fluoride, zirconium fluoride, silver fluoride, cetylamine hydrofluoride, glycine hydrochloride, lysine hydrofluoride, alanine hydrofluoride, stannous fluoride, stannous chloride fluoride and mixtures thereof.

19. The composition as claimed in claim 1, wherein the lytic enzymes are derived from organisms selected from the group consisting of Streptomyces griseus, Streptomyces diastatochromagenes, Streptomyces farinosus, Chalaropsis, Flavobacterium, Myxobacter, Staphylcoccus epidermidis, Micrococcus, Pseudomonas aetuginosa, Aeromanas, Streptomyces albus and Streptomyces globisporus; the bacteriocins are derived from organisms selected from the group consisting of Enterobactor cloacase, Escherichia coli, Proteus mirabilis, Pseudomonas aeruginosa, Streptococcus mutans and Staphylococcus staphylolyticus; the GTF inhibitors are derived from organisms selected from the group consisting of Arthrinum sp., Fusarinum sp., Macrophomina sp., Micromonospora sp., Gnomoniella sp., Nodulisporium sp., Aspergillus sp., and Bacillus sp.; and the dextranases are derived from organisms selected from the group consisting of Chaetomium sp., Streptomyces sp., Bacillus sp. and Corynebacterium.

20. The caries-preventive composition as claimed in claim 1, which is in a form selected from the group consisting of toothpastes, toothpowders, mouthwashes, dental pastes, gingivl massage creams, gargle tablets, troches, chewing gums, ice-creams and whipped creams.

21. The composition as claimed in claim 1, which comprises 0.0002 to 10% by weight of the antibody to the total weight of said oral composition and at least one synergist component in the composition selected from the group consisting of 0.0001 to 0.1 wt% fluorine, 0.1 to 1000 ppm chlorhexidine and salts thereof; 0.0001 to 10 wt% of lytic enzymes, bacteriocins, glucosyltransferase inhibitors, proteases and dextranases.

22. The composition as claimed in claim 21, which comprises 0.002 to 5% by weight of antibody to the total weight of said oral composition and at least one synergist component in the composition selected from the group consisting of 0.0001 to 0.001 wt% fluorine, 10 to 100 ppm chlorhexidine and salts thereof, 0.001 to 5 wt% of lytic enzymes, bacteriocins, gluosyltransferase inhibitors, proteases and dextranases.

23. The composition as claimed in claim 1, further comprising an abrasive in an amount of 5 to 95% by weight of the composition selected from the group consisting of calcium secondary phosphate dihydrate, calcium secondary phosphate anhydrate, calcium primary phosphate, calcium tertiary phosphate, calcium carbonate, calcium pyrophosphate insoluble sodium metaphosphate, amorphous silica, crystal silica, aluminosilicate, aluminum oxide, aluminum hydroxide, magnesium tertiary phosphate, magnesium carbonate, calcium sulfate and titanium dioxide.

24. The composition as claimed in claim 1, further comprising
   0.3 to 5% by weight of the composition of a binder selected from the group consisting of sodium carboxymethyl cellulose, methyl cellulose, sodium carboxymethyl hydroxyethyl cellulose, hydroxyethyl cellulose, sodium alginate, carrageenan, gum arabic, xanthan gum, tragacanth gum, karaya gum, polyvinylalcohol, sodium polyacrylate, carboxyvinyl polymer and polyvinyl pyrrolidone; or
   10 to 70% by weight of the composition of a humectant selected from the group consisting of polyethylene glycol, ethylene glycol, sorbitol, glycerol, poropylene glycol, 1,3-butylene glycol, xylitol, maltitol and lactitol; or
   0 to 10% by weight of the composition of a surface active agent selected from the group consisting of water soluble salts of alkyl sulfate having 8 to 18 carbon atoms, sodium salts of higher fatty acids, water-soluble salts of sulfonated monoglycerides of higher fatty acids having 10 to 18 carbon atoms in the fatty acid group, sucrose fatty acid esters having 12 to 18 carbon atoms in the fatty acid group, monolauryl ester and betaine and amino acid type amphoteric surfactants; or mixtures of said binder, humectant and surface active agent.

25. The composition as claimed in claim 1, further comprising:
   an effective amount of a flavor selected from the group consisting of peppermint oil and spearmint oil; or
   a flavoring material selected form the group consisting of l-menthol, carvone, eugenol and anethole; or
   a sweetener selected from the group consisting of sodium saccharinate, stevioside, neohesperidylidyhydrochalcone, glycyrrhizin, perillartine and p-methoxycinnamic aldehyde; or
   a preservative or
   mixtures of said flavor, flavoring material, sweetener and preservative.

26. The composition as claimed in claim 1, further comprising an effective amount of ingredients selected from the group consisting of mutanase, sorbic acid, alexidine hinoktiol, cetylpyridinium chloride, alkyl glycine, alkyldiaminoethyl glycinate, allantoin, ε-aminocaprioc acid, tranexamic acid azulene, vitamin E, a water soluble primary phosphate, a water secondary phosphate, a quaternary ammonium compound, sodium chloride, crude drugs and mixtures thereof.

27. The composition as claimed in claim 1, wherein said composition is a paste like or liquid oral composition having a pH ranging from 5 to 10.

* * * * *